US012793216B2

(12) United States Patent
Grimm et al.

(10) Patent No.: US 12,793,216 B2
(45) Date of Patent: Nov. 10, 2026

(54) SYSTEMS AND METHODS FOR ANALYSING DIGITAL IMAGES

(71) Applicant: Hoffmann-La Roche Inc., Little Falls, NJ (US)

(72) Inventors: Oliver Heinrich Grimm, Copenhagen (DK); Lucy Grace Hutchinson, Basel (CH)

(73) Assignee: Hoffman-La Roche Inc., Little Falls, NJ (US)

( * ) Notice: Subject to any disclaimer, the term of this patent is extended or adjusted under 35 U.S.C. 154(b) by 267 days.

(21) Appl. No.: 18/644,063

(22) Filed: Apr. 23, 2024

(65) Prior Publication Data

US 2024/0281967 A1 Aug. 22, 2024

Related U.S. Application Data

(63) Continuation of application No. PCT/EP2022/079505, filed on Oct. 24, 2022.

(30) Foreign Application Priority Data

Oct. 25, 2021 (EP) .................................... 21204437

(51) Int. Cl.

| | |
|---|---|
| ***G06T 7/00*** | (2017.01) |
| ***G06T 7/12*** | (2017.01) |
| ***G06V 10/764*** | (2022.01) |
| ***G16H 30/40*** | (2018.01) |

(52) U.S. Cl.

CPC .............. *G06T 7/0012* (2013.01); *G06T 7/12* (2017.01); *G06V 10/764* (2022.01); *G16H 30/40* (2018.01); *G06T 2207/30024* (2013.01); *G06T 2207/30096* (2013.01)

(58) Field of Classification Search

CPC ..................... G06T 7/0012; G06T 7/12; G06T 2207/30024; G06T 2207/30096; G06T 7/0016; G06T 2207/20081; G06T 2207/20084; G06T 7/11; G06T 2207/10072; G06T 2207/20021; G06T 2207/30004; G16H 30/40; G16H 30/00; G06V 10/764

See application file for complete search history.

(56) References Cited

U.S. PATENT DOCUMENTS

| | | | | |
|---|---|---|---|---|
| 10,991,097 B2 * | 4/2021 | Yip | ........................ | G06T 7/0012 |
| 11,508,120 B2 * | 11/2022 | Yu | .............................. | G06T 7/70 |
| 11,830,621 B2 * | 11/2023 | LeBoeuf | ................ | A61B 34/10 |
| 2017/0076448 A1 * | 3/2017 | Chen | ......................... | G06T 7/12 |

(Continued)

OTHER PUBLICATIONS

Bussola, N., Papa, B., Melaiu, O., Castellano, A., Fruci, D., & Jurman, G. (2021). Quantification of the Immune Content in Neuroblastoma: Deep Learning and Topological Data Analysis in Digital Pathology. International journal of molecular sciences, 22(16), 8804. (Year: 2021).*

(Continued)

*Primary Examiner* — Vu Le
(74) *Attorney, Agent, or Firm* — MORRISON & FOERSTER LLP

(57) ABSTRACT

Systems and methods disclosed herein relate generally to object modeling in digital images, applicable in clinical histological imaging data for modeling spatial biomarkers dynamics in cancer immunotherapy.

20 Claims, 8 Drawing Sheets

(56) References Cited

U.S. PATENT DOCUMENTS

| | | | | |
|---|---|---|---|---|
| 2019/0087954 | A1* | 3/2019 | Lloyd | G06T 7/0012 |
| 2020/0211189 | A1* | 7/2020 | Yip | G06T 7/0012 |
| 2024/0371184 | A1* | 11/2024 | Comiter | G06N 3/0475 |

OTHER PUBLICATIONS

Alfonso, J. C. L. et al. In-silico insights on the prognostic potential of immune cell infiltration patterns in the breast lobular epithelium Open. https://doi.org/10.1038/srep33322 (2016). (Year: 2016).*

Klauschen, F., Müller, K. R., Binder, A., Bockmayr, M., Hägele, M., Seegerer, P., . . . & International Immuno-Oncology Biomarker Working Group. (Oct. 2018). Scoring of tumor-infiltrating lymphocytes: From visual estimation to machine learning. In Seminars in cancer biology (vol. 52, pp. 151-157). (Year: 2018).*

Schwen, L. O., Andersson, E., Korski, K., Weiss, N., Haase, S., & Gaire, F. (2018). Data-Driven Discovery of Immune Contexture Biomarkers. Front Oncol. 2018; 8: 627-. (Year: 2018).*

Kather, J. N. et al. In silico modeling of immunotherapy and stroma-targeting therapies in human colorectal cancer. Cancer Res. 77, 6442-6452 (2017). (Year: 2017).*

Wang, D., Khosla, A., Gargeya, R., Irshad, H., & Beck, A. H. (2016). Deep learning for identifying metastatic breast cancer. arXiv preprint arXiv:1606.05718. (Year: 2016).*

Cui, L., Li, H., Hui, W., Chen, S., Yang, L., Kang, Y., Bo, Q., & Feng, J. (2020). A deep learning-based framework for lung cancer survival analysis with biomarker interpretation. BMC bioinformatics, 21(1), 112. https://doi.org/10.1186/s12859-020-3431-z (Year: 2020).*

Yu, K. H., Zhang, C., Berry, G. J., Altman, R. B., Ré, C., Rubin, D. L., & Snyder, M. (2016). Predicting non-small cell lung cancer prognosis by fully automated microscopic pathology image features. Nature communications, 7, 12474. https://doi.org/10.1038/ncomms12474 (Year: 2016).*

Alfonso, J., et al., "In-silico insights on the prognostic potential of immune cell infiltration patterns in the breast lobular epithelium" Nat Sci Rep 6:33322 (1-18) (Sep. 23, 2016).

Barua, S., et al., "Spatial interaction of tumor cells and regulatory T cells correlates with survival in non-small cell lung cancer" Lung Cancer 117:73-79 (Mar. 1, 2018).

Brown, J., et al., "Quantitative assessment Ki-67 score for prediction of response to neoadjuvant chemotherapy in breast cancer" Lab Invest 94(1):98-106 (Jan. 1, 2014).

Corredor, G., et al., "Spatial Architecture and Arrangement of Tumor-Infiltrating Lymphocytes for Predicting Likelihood of Recurrence in Early-Stage Non-Small Cell Lung Cancer" Clin Cancer Res 25(5):1526-1534 (Mar. 1, 2019).

De Matos, J., et al., "Machine Learning Methods for Histopathological Image Analysis: A Review" Electronics 10(5):562 (1-42) (Feb. 27, 2021).

Fu, M., "Optimization via simulation: A review" Ann Operation Res 53(1):199-247 (Dec. 1, 1994).

Gong, C., et al., "A computational multiscale agent-based model for simulating spatio-temporal tumour immune response to PD1 and PDL 1 inhibition" J R Soc Interface 14(134):20170320 (1-13) (Sep. 1, 2017).

Hutchinson, L., et al., "Integrating digital pathology and mathematical modelling to predict spatial biomarker dynamics in cancer immunotherapy" NPJ Digital Med 5(1):92 (1-13) (Jul. 12, 2022).

"International Preliminary Report on Patentability—PCT/EP2022/079505" (Report Issuance Date: Apr. 30, 2024; Chapter I), :pp. 1-10 (May 10, 2024).

"International Search Report—PCT/EP2022/079505" (w/Written Opinion), :pp. 1-16 (Mar. 13, 2023).

Kather, J., et al., "In Silico Modeling of Immunotherapy and Stroma-Targeting Therapies in Human Colorectal Cancer" Cancer Res (Epub: Sep. 18, 2017), 77(22):6442-6452 (Nov. 15, 2017).

Kather, J., et al., "Topography of cancer-associated immune cells in human solid tumors" ELIFE 7:e36967 (1-35) (Sep. 4, 2018).

Klauschen, F., et al., "Scoring of tumor-infiltrating lymphocytes: From visual estimation to machine learning" Semin Cancer Biol (Epub: Jul. 7, 2018), 52(PT 2):151-157 (Oct. 1, 2018).

Kun-Hsing, Y., et al., "Predicting non-small cell lung cancer prognosis by fully automated microscopic pathology image features" Nat Commun 7(12474):1-10 (Aug. 16, 2016).

Norton, K., et al., "Multiscale Agent-Based and Hybrid Modeling of the Tumor Immune Microenvironment" Processes—Basel 7(1):37 (1-23) (Jan. 13, 2019).

Saltz, J., et al., "Spatial Organization and Molecular Correlation of Tumor-Infiltrating Lymphocytes Using Deep Learning on Pathology Images" Cell Reports 23(1):181-193.e7 (Apr. 3, 2018).

Schwen, L., et al., "Data-Driven Discovery of Immune Contexture Biomarkers" Front Oncol 8:627 (1-15) (Dec. 18, 2018).

* cited by examiner

SYSTEMS AND METHODS FOR ANALYSING DIGITAL IMAGES

CROSS-REFERENCE TO RELATED APPLICATIONS

This application is a Continuation of International Application No. PCT/EP2022/079505, filed Oct. 24, 2022, which claims benefit of priority to European Patent Application No. 21204437.4 filed Oct. 25, 2021, each of which is incorporated herein by reference in its entirety.

The present invention relates to object modeling in digital images. Various embodiments of the present invention relate to systems and methods for object modeling in clinical histological imaging data and, more specifically but not limited, to systems and methods for modeling spatial biomarkers dynamics in cancer immunotherapy.

During early phase oncology clinical trials it is of the utmost importance to verify the mode of action of a drug by investigating treatment effects in the tumor tissue by histological methods. Typically, a first biopsy is taken before the treatment, and a second biopsy on-treatment. Digitized versions of the pre-stained biopsy tissue sections can be analyzed with several digital pathology methods, ranging from statistical analysis to machine-learning models. Spatial biomarkers derived from immunohistochemistry images of tumor biopsies have shown[1,2,3,4,5] to contain information that is predictive of prognosis, tumor recurrence or response to treatment.

To ensure meaningful conclusions regarding the mode of action, the time point at which the biopsies are taken is crucial. Currently, this time point is chosen by clinical experts on a best-guess basis. Mechanistic models exist[6,7] that reproduce spatial features of cells in biopsies via simulation of tumor-immune cells interactions. Integrating digital pathology and such mechanistic disease models would help to gain insights into spatial biomarker dynamics. However, existing models are difficult to be optimized, as they either are validated only qualitatively with a visual comparison between simulated and observed spatial features[6,8,9] or quantitatively within the scope of the simulated images only[10]. Thus there is a need for a quantitative scientific approach for optimizing mathematical models, that can be validated and reliably applied to improve clinical trial design, including but not limited to the appropriate scheduling of on-treatment biopsies, the identification of the best treatments or treatment combinations, and/or the adaptation of the clinical trial on a personalized or a cohort basis. Further limitations and disadvantages of current approaches will become apparent to the skilled in the art, through comparison of the features of the prior art with some aspects of the present invention, as set forth in the remainder of the present invention and with reference to the drawings.

DETAILED DESCRIPTION

Figure 1:
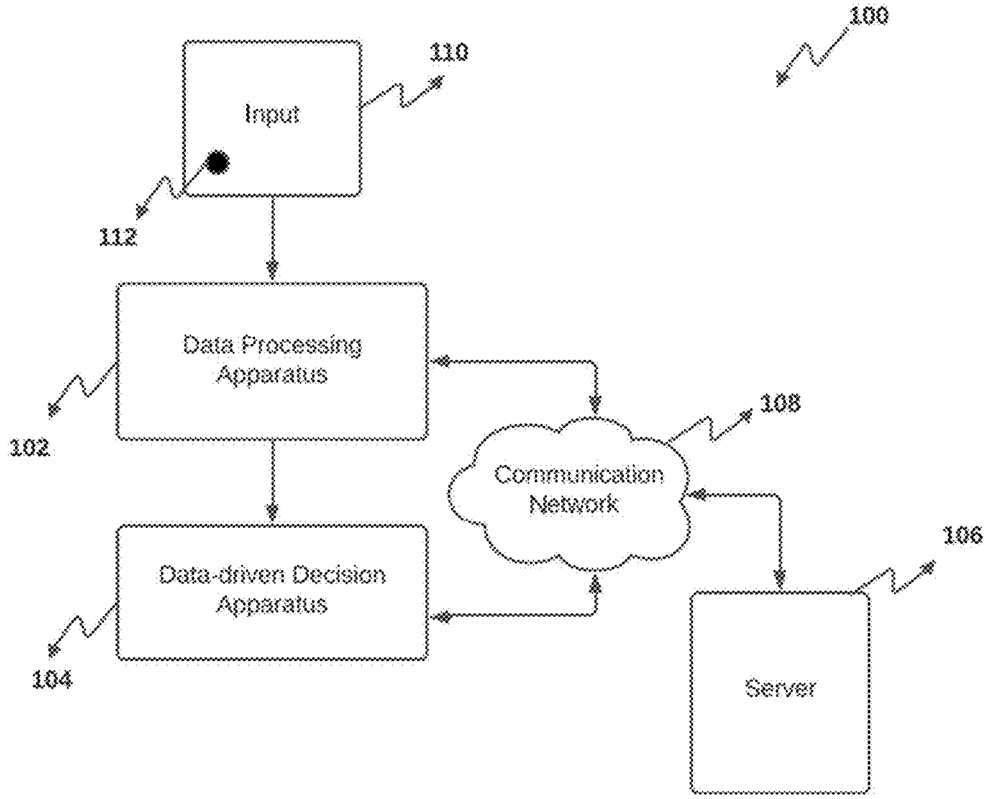
FIG. 1 illustrates an exemplary instance of a system for optimizing the parameter values of a parameter-based model using for example a spatial agreement measure, in accordance with an embodiment of the disclosure.

The present invention relates to object modeling in digital images. Various embodiments of the present invention relate to systems and methods for object modeling in clinical histological imaging data and, more specifically but not limited, to systems and methods for modeling spatial biomarkers dynamics in cancer immunotherapy.

The following described implementations refer to aspects of the disclosed systems and methods employed to integrate digital pathology and mathematical modeling. The disclosed digital pathology methods to classify and segment one or more objects of interest in an image can comprise the application of one or more trained Artificial Neural Networks (ANNs) or supervised Neural Networks, whereby the networks are trained on images containing one or more objects of interest with accompanying labelling metadata. When applied to oncology clinical histological data, these networks are trained on clinical histological images manually pre-annotated by pathologists. It may be evident to the person skilled in the art that the disclosed systems and methods can be adapted to the implementation of unsupervised Neural Networks, thus avoiding the need for performing pre-annotation of the large training dataset of images. The disclosed mathematical models to simulate the spatial distribution of objects of interest in an image can comprise the application of agent-based models. When applied to oncology clinical histological data, these models can comprise two populations of agents: tumor cells and immune cells, laid out on a grid, which behave according to prescribed rules and capture emergent spatial dynamics. When digital images from paired biopsies captured pre-treatment and on-treatment respectively are fed as input to the disclosed systems and methods, the dynamic component of the models can be validated using the spatial and temporal resolution.

As known to the person skilled in the art, a biopsy is defined as an examination of tissue removed from a living body to discover the presence, cause, or extent of a disease. As used in the present invention, the term paired biopsies refers to biopsies obtained from the same patient at different points in time. According to some embodiments of the present invention, the paired biopsies can refer to biopsies obtained pre-treatment and on-treatment from a patient undergoing a treatment. When applied to oncology clinical histological images, such treatments can be real or hypothetical cancer immunotherapies, comprising both monotherapies and combinations of monotherapies. As used in the present invention, a monotherapy is a therapy carried out with a single drug.

As known to the person skilled in the art, the CD8 acronym stands for cluster of differentiation 8, and CD8+ is used to refer to cytotoxic T-cells, also known in the literature as cytotoxic T lymphocytes, or CTLs. As used in the present invention and as known to the person skilled in the art, proliferating tumor cells that express the Ki67 marker are cells that have the Ki67 protein present during all active phases of their cycle.

As used in the present invention and as established in mathematics, the Chebyshev radial distance, also known as maximum metric, is a metric defined on a vector space where the distance between two vectors is the greatest of their differences along any coordinate dimension. The radial distribution function, or pair correlation function, in a system of objects describes how density varies as a function of the mutual distance between objects in the system. When referring to the extraction of the radial distribution function and/or the spatial agreement measure in the present invention, the term distance is used with the meaning of mutual distance between objects.

Further, the term distance units as used in the present invention refers to the chosen grid size, which when applied to oncology clinical histological images is typically equal to the immune cell width.

FIG. 1 illustrates an exemplary instance of a system for optimizing the parameter values of a parameter-based model using for example a spatial agreement measure, in accordance with an embodiment of the disclosure. With reference to FIG. 1, the system 100 can include a data processing apparatus 102, a data-driven decision apparatus 104, a server 106 and a communication network 108. The data processing apparatus 102 can be communicatively coupled to the server 106 and the data-driven decision apparatus 104 via the communication network 108. In other embodiments, the data processing apparatus 102 and the data-driven decision apparatus 104 can be embedded in a single apparatus. The data processing apparatus 102 can receive as input a set of one or more images 110 containing at least one object of interest 112. In other embodiments, the set of images 110 can be stored in the server 106 and sent from the server 106 to the data processing apparatus 102 via the communication network 108.

The data processing device 102 can be designed to receive the input set of images 110 and sequentially perform classification and segmentation of the at least one object of interest 112 in the input set of images 110 via at least one machine-learning model. In another embodiment, the data processing device 102 can be configured to perform in parallel the classification and the segmentation of the at least one object of interest 112 in the input set of images 110 via a single machine-learning model. The data processing device 102 can perform the tiling of the input set of images 110 and the mapping on a grid of the tiles. The data processing device 102 can allow for the extraction of features, including but not limited to position and radial distribution function of the one or more objects of interest. The data processing device 102 can receive at least one set of parameter values and run via a parameter-based model at least one simulation at a second point in time of the mapped tiles of one image of the input set captured at a first point in time. The data processing device 102 can allow for the extraction of features in the simulated tiles, including but not limited to position and radial distribution function of the one or more objects of interest. The data processing device 102 can allow for the extraction of some metric, including but not limited to a spatial agreement measure to compare the radial distribution functions of the one or more objects of interest in the simulated tiles at the second point in time and the radial distribution functions of the one or more objects of interest in the tiles of the received image in the input set of images 110 captured at the same second point in time as the simulated tiles. Examples of the data processing device 102 include but are not limited to a computer workstation, a handheld computer, a mobile phone, a smart appliance.

The data-driven decision apparatus 104 can comprise software, hardware or various combinations of these. The data-driven decision apparatus 104 can be designed to receive parameters and features outputted by the data processing device 102 and in an embodiment, to assign the calculated spatial agreement measures between simulated and received images to the corresponding sets of parameter values inputted to the simulation model to obtain the simulated images. In an embodiment, the data-driven decision apparatus 104 can be able to access from the server 106 the sets of parameter values inputted to the simulation model to obtain the simulated images. In an embodiment, the data-driven decision apparatus 104 can be able to access from the server 106 the stored features of objects, extracted while processing different images comprising the object, whereby these different images can have been recorded and annotated at different points in time. Thus in said embodiment the data-driven decision apparatus 104 can allow for an assessment of the temporal evolution of the object features. In the case of clinical histological digital images, the assessment of the temporal evolution of the object features can translate into an assessment of the temporal evolution of biomarkers. Examples of the data-driven decision apparatus 104 include but are not limited to computer workstation, a handheld computer, a mobile phone, a smart appliance.

The server 106 can be configured to store the training imaging datasets for the at least one trained machine-learning model implemented in the data processing device 102. In some embodiments, the server 106 can also store metadata related to the training data. The server 106 can also store the input set of images 110 as well as some metadata related to the input set of images 110. The server 106 can be designed to send the input set of images 110 to the data processing apparatus 102 via the communication network 108, and/or to receive the output parameters and features of the input set of image 110 from the data processing apparatus 102 via the communication network 108. In an embodiment, the server 106 can be configured to receive and store the sets of parameter values inputted to the simulation model run by the data processing apparatus 102. The server 106 can also be configured to receive and store the metrics associated with the object features and/or the input set of images at an intermediate processing state, for example the mapped tiles, from the data-driven decision apparatus 104 via the communication network 108. Examples of the server 106 include but are not limited to application servers, cloud servers, database servers, file servers, and/or other types of servers.

The communication network 108 can comprise the means through which the data processing apparatus 102, the data-driven decision apparatus 104 and the server can be communicatively coupled. Examples of the communication network 108 include but are not limited to the Internet, a cloud network, a Wi-Fi network, a Personal Area Network (PAN), a Local Area Network (LAN) or a Metropolitan Area Network (MAN). Various devices of the system 100 can be configured to connect with the communication network 108 with wired and/or wireless protocols. Examples of protocols include but are not limited to Transmission Control Protocol/Internet Protocol (TCP/IP). Hypertext Transfer Protocol (HTTP). File Transfer Protocol (FTP), Bluetooth (BT). The at least one trained machine-learning model can be deployed on the data processing apparatus 102 and can be configured to output classes, bounding boxes and masks for each object, as well as extracted features of the said objects from the input images fed to the trained DNN. The at least one trained machine-learning model can include a plurality of interconnected processing units, also referred to as neurons, arranged in at least one hidden layer plus an input layer and an output layer. Each neuron can be connected to other neurons, with connections modulated by weights.

Prior to deployment on the data processing apparatus 102, the at least one trained machine-learning model can be obtained through a training process on a DNN architecture initialized with random weights. The training dataset can include pairs of images and their metadata, e.g. pre-annotated images in the case of clinical histological digital images. The metadata can comprise the number and position of objects in the images, as well as a shallow or detailed object classification. In an embodiment, the annotation can be performed manually by pathologists. In another embodiment, the training process is performed on a DNN architecture with a training dataset of unlabelled images. Unlabelled images can be images without any associated metadata. The DNN architecture can learn the output features of said unlabelled images via an unsupervised learning process. In an exemplary embodiment, the training dataset can be stored in the server 106 and/or the training process can be performed by the server 106.

In some embodiments, the trained DNN can be a trained Convolutional Neural Network (CNN). Processing units in the early layers of CNNs learn to activate in response to simple local features, for example patterns at particular orientations or edges, while units in the deeper layers combine the low-level features into more complex patterns. Region based CNNs (R-CNNs) extract region proposals where the object of interest can be located and then apply CNNs to classify the object and locate it within the region proposal by defining a bounding box around it. In other embodiments, a Faster Region Based Convolutional Neural Network (Faster R-CNN) can be employed for the identification of a proposed Region of Interest (RoI) as well as for object detection, while a mask CNN comprising two CNNs can be employed for the object segmentation to output a binary mask. In another embodiment, a Mask R-CNN can replace the Faster R-CNN and mask CNN, with the capability of performing the object segmentation in parallel with the object detection, resulting in improved processing speed and improved accuracy especially in detecting overlapping objects.

The set of parameters and assigned spatial agreement measure values produced by the data-driven decision apparatus 104 can be deployed on the server 106 to be added to the training dataset for a further training process of the network. Images with spatial agreement measure values as their associated metadata provided by the data-driven decision apparatus 104 can be used as an alternative training dataset for a supervised learning process. In some other embodiments, all functionalities of the data-driven decision apparatus 104 are implemented in the data processing apparatus 102.

Figure 2:
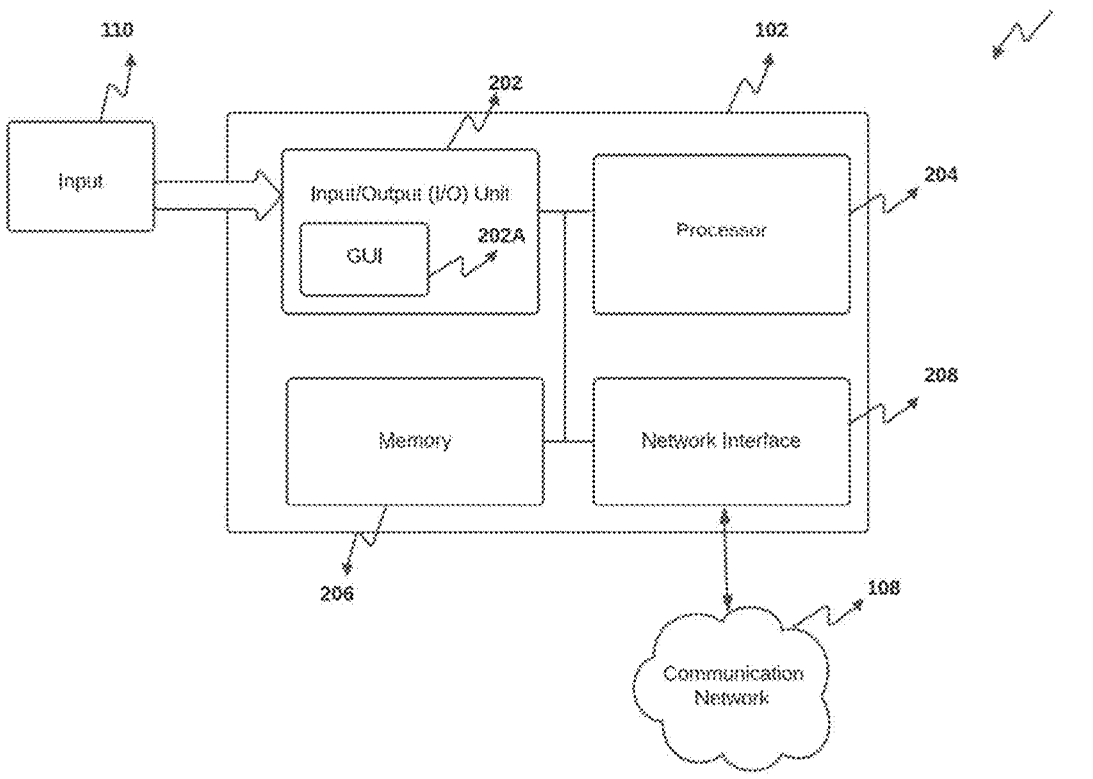
FIG. 2 depicts a block diagram that illustrates an exemplary data processing apparatus for optimizing the parameter values of a parameter-based model using for example a spatial agreement measure, in accordance with an embodiment of the disclosure.

FIG. 2 depicts a block diagram that illustrates an exemplary data processing apparatus for optimizing the parameter values of a parameter-based model using for example a spatial agreement measure, in accordance with an embodiment of the disclosure. FIG. 2 is explained in conjunction with elements from FIG. 1. With reference to FIG. 2, it is shown a block diagram 200 of the data processing apparatus 102. The data processing apparatus 102 may include an Input/Output (I/O) unit 202 further comprising a Graphical User Interface (GUI) 202A, a processor 204, a memory 206 and a network interface 208. The processor 204 may be communicatively coupled with the memory 206, the I/O unit 202, the network interface 208. In one or more embodiments, the data processing apparatus 102 may also include provisions to correlate the results of the data processing with one or more metrics, for example a spatial agreement measure.

The I/O unit 202 may comprise suitable logic, circuitry and interfaces that may act as interface between a user and the data processing apparatus 102. The I/O unit 202 may be configured to receive an input set of images 110 containing at least one object of interest 112. The I/O unit 202 may include different operational components of the data processing apparatus 102. The I/O unit 202 may be programmed to provide a GUI 202A for user interface. Examples of the I/O unit 202 may include, but are not limited to, a touch screen, a keyboard, a mouse, a joystick, a microphone, and a display screen, like for example a screen displaying the GUI 202A.

The GUI 202A may comprise suitable logic, circuitry and interfaces that may be configured to provide the communication between a user and the data processing apparatus 102. In some embodiments, the GUI may be displayed on an external screen, communicatively or mechanically coupled to the data processing apparatus 102. The screen displaying the GUI 202A may be a touch screen or a normal screen.

The processor 204 may comprise suitable logic, circuitry and interfaces that may be configured to execute programs stored in the memory 206. The programs may correspond to sets of instructions for image processing operations, including but not limited to object classification and segmentation. In some embodiments, the sets of instructions also include the object characterization operation, including but not limited to feature extraction. In an embodiment, the programs may comprise sets of instructions for image simulation operations, including but not limited to object dynamics modeling. In an embodiment, the programs may comprise sets of instructions for metric evaluations, for example evaluation of a spatial agreement measure to be assigned to a pair of simulated and received image. The processor 204 may be built on a number of processor technologies known in the art. Examples of the processor 204 may include, but are not limited to. Graphical Processing Units (GPUs), a Central Processing Units (CPUs), motherboards, network cards.

The memory 206 may comprise suitable logic, circuitry and interfaces that may be configured to store programs to be executed by the processor 204. Additionally, the memory 206 may be configured to store the input set of images 110 and/or its associated metadata. In another embodiment, the memory may store a subset of or the entire training dataset, comprising in some embodiments the input set of images and their associated metadata. Examples of the implementation of the memory 206 may include, but are not limited to, Random Access Memory (RAM), Read Only Memory (ROM), Hard Disk Drive (HDD). Solid State Drive (SDD) and/or other memory systems.

The network interface 208 may comprise suitable logic, circuitry and interfaces that may be configured to enable the communication between the data processing apparatus 102, the data-driven decision apparatus 104 and the server 106 via the communication network 108. The network interface 208 may be implemented in a number of known technologies that support wired or wireless communication with the communication network 108. The network interface 208 may include, but is not limited to, a computer port, a network interface controller, a network socket or any other network interface systems.

Figure 3:
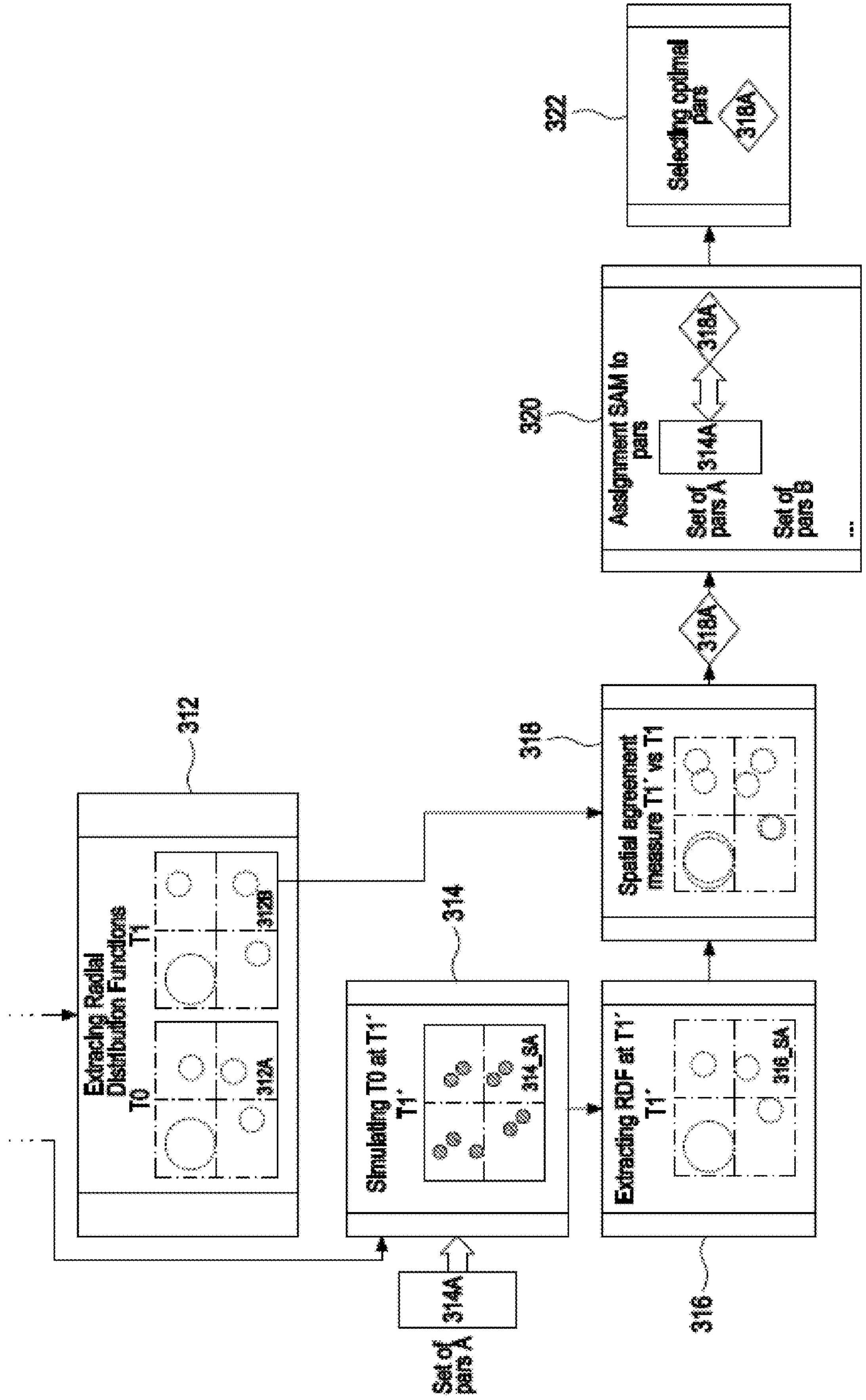
FIG. 3 depicts a flow chart that illustrates an exemplary method for optimizing the parameter values of a parameter-based model using for example a spatial agreement measure, in accordance with an embodiment of the disclosure.
Figure 3:
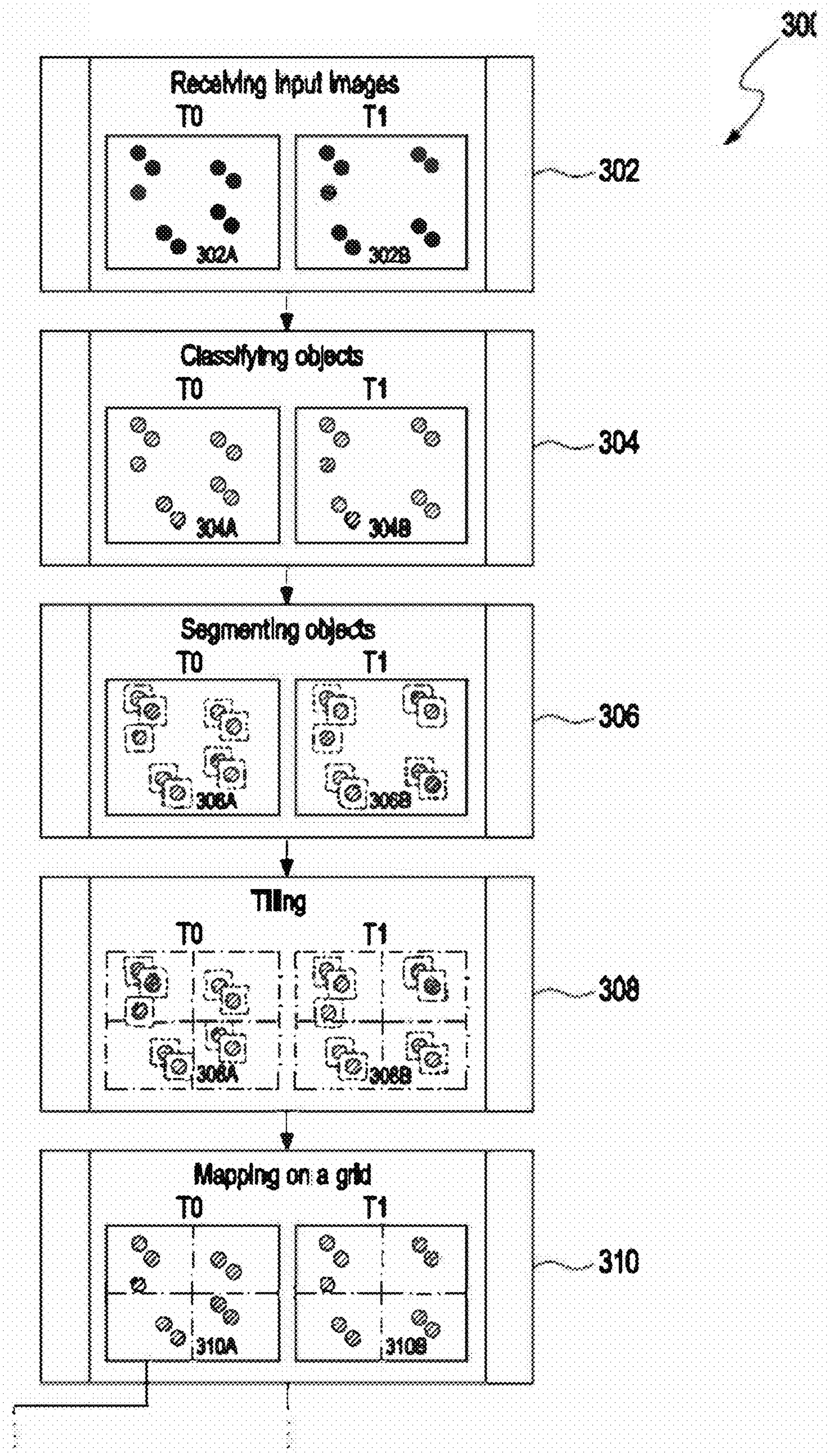

FIG. 3 depicts a flow chart that illustrates an exemplary method for optimizing the parameter values of a parameter-based model using for example a spatial agreement measure, in accordance with an embodiment of the disclosure. With reference to FIG. 3, an exemplary flow chart 300 is shown.

At 302 at least two input images 302A and 302B can be received, wherein each image comprises the same one or more objects of interest captured at points in time T0 and T1 respectively. The input images can be digitized images from paired biopsies of one tumor patient obtained at two time points, for example pre-treatment and on-treatment.

At 304, a first machine-learning model can be executed. The machine-learning model can be fed with the input images to classify the one or more objects of interest. In FIG. 3, the input images with classified objects of interest are indicated as 304A and 304B. The machine-learning model can be an Artificial Neural Network (ANN), a Deep Neural Network (DNN), and/or a chain of DNNs. In some embodiments, the machine-learning model can comprise a Convolutional Neural Network (CNN), and/or a chain of CNNs. The one or more objects of interest can be tumor cells and/or immune cells. Immune cells can be cytotoxic CD8+ T-cells, proliferating or non proliferating. The tumor cells can be proliferating, and can be expressing Ki67 as the marker of cell proliferation.

At 306, a second machine-learning model can be executed. The machine-learning model can be fed with the input images to segment the one or more objects of interest. In FIG. 3, the input images with classified and segmented objects of interest are indicated as 306A and 306B. The machine-learning model can be an Artificial Neural Network (ANN), a Deep Neural Network (DNN), and/or a chain of DNNs. In some embodiments, the machine-learning model can comprise a Convolutional Neural Network (CNN), and/or a chain of CNNs. In some embodiments, the machine-learning model can comprise Region-based CNNs (R-CNNs), Fast or Faster R-CNNs and/or Mask R-CNNs. In some embodiments, 304 and 306 can be performed by a single machine-learning model.

At 308, a tiling algorithm can be executed. The input images can be divided into minimally overlapping square tiles. In FIG. 3, the input images with classified and segmented objects of interest divided in tiles are indicated as 308A and 308B. The tile overlap can be set to be smaller or equal to 10% of the tile size. When the one or more objects of interest are tumor or immune cells, with CD8+ T-cells having a width of approximately 5 micrometers, the tile size can be set to 100×100 immune cell widths.

At 310, a mapping algorithm can be executed. The tiles obtained at 308 can be mapped on a grid, with each object of interest located on a grid site. In FIG. 3, the input images with classified objects of interest divided in tiles and mapped on a grid are indicated as 310A and 310B. When the one or more objects of interest are tumor or immune cells, with CD8+ T-cells having a width of approximately 5 micrometers, the size of each grid cell can be set equal to the immune cell width. The mapping algorithm stores the position of the tumor and immune cells on the grid, as well as physiological properties of the cells, including but not limited to proliferation capacity and stem cellness.

At 312, Radial Distribution Functions (RDFs) can be extracted in each mapped tile of the images 310A and 310B. In FIG. 3, the images divided in tiles and mapped on a grid with a RDF in each tile are indicated as 312A and 312B. From each object, the Chebyshev radial distance to every other object can be computed, and a histogram can be obtained for the total number of objects within each binned range of radial distances. The histogram can be normalized to the mean density of objects on the tile. The RDF can give an indication of the spatial distribution of the objects in the tile. When the one or more objects of interest are tumor or immune cells, the RDFs can be extracted for both types of cells separately.

At 314, a parameter-based model with set of parameters A 314A can be fed with the mapped tiles of the input image 310A captured at time point T0 and used to simulate the positions of the objects within the mapped tiles of the input image at a different time point, for example T1. In FIG. 3, the notation T1' is used for the simulated image at time point T1. Simulated images can be generated and stored at 24 hours intervals. In the parameter-based model at 314, each object can proliferate, migrate, die or interact with other objects according to probabilistic rules. The likelihood of an object to perform an action can be calculated based on probability distributions and its local neighbourhood. When the one or more objects of interest are tumor or immune cells, in order for an immune cell to kill a tumor cell they must be for example in physical proximity. The model parameters can be chosen based on a sensitivity analysis, for example by varying each model parameter within physiological ranges and recording the immune and tumor cell count at a T1 corresponding to 20 days. The high-sensitivity model parameters can be found to be those related to immune cell dynamics, including but not limited to immune cell proliferation, natural death, killing as well as the randomness of cell migration and the influx rate of immune cells. Several sets of parameter values, for example set A 314A, set B, . . . , can be used to define the parameter-based model. For example, 1000 randomly generated parameter values for the chosen model parameters can be used to run 1000 simulations. In FIG. 3, the image 310A with mapped tiles simulated at time point T1' with set A is indicated as 314_SA.

At 316, Radial Distribution Functions (RDFs) can be extracted in each mapped tile of the simulated images, as illustrated for 314_SA. In FIG. 3, the image 314_SA with a RDF in each tile is indicated as 316_SA.

At 318, a Spatial Agreement Measure (SAM) can be calculated based on the overlap between the RDFs in each tile of image 312B at T1 and the RDFs in each tile of each image simulated at T1', as illustrated for 316_SA. The SAM for comparing simulated and observed sets of tiles can be defined as the proportion of the distances for which more than 80% of RDF values of the simulated tile set fit within the range approximately of 20% of the RDFs of the observed tile set. In FIG. 3, the SAM value calculated is indicated as 318A. When the one or more objects of interest are tumor or immune cells, SAM defines a derived spatial statistics that can overcome the variability of the stochastic nature of biological processes. At 318, a further processing (VarSAM) can be performed to capture the variability of spatial distributions, by providing extra weight to the observed cell density within a short radius of a given immune cell. The VarSAM can identify artificially high SAM values that result from narrow RDFs.

At 320, SAM values obtained at 318 can be assigned to the corresponding set of parameter values inputted to the model at 314. Sets of parameter values can be ranked based on the assigned SAM value.

At 322, the optimal set of parameter values can be selected as the set assigned to the maximum calculated SAM value. In some embodiments, the performance of the optimal set of parameter values can be validated using a test dataset separate from the training dataset used to optimize the model. In some embodiments, the 12 highest-ranked sets of parameter values can be selected as optimal sets, rather than identifying one top-performing set. Optimal sets of parameter values can be chosen based on the SAM value as well as the VarSAM value, for example with a SAM value greater than 0.7 and a VarSAM value greater than 0.3.

Figure 4:
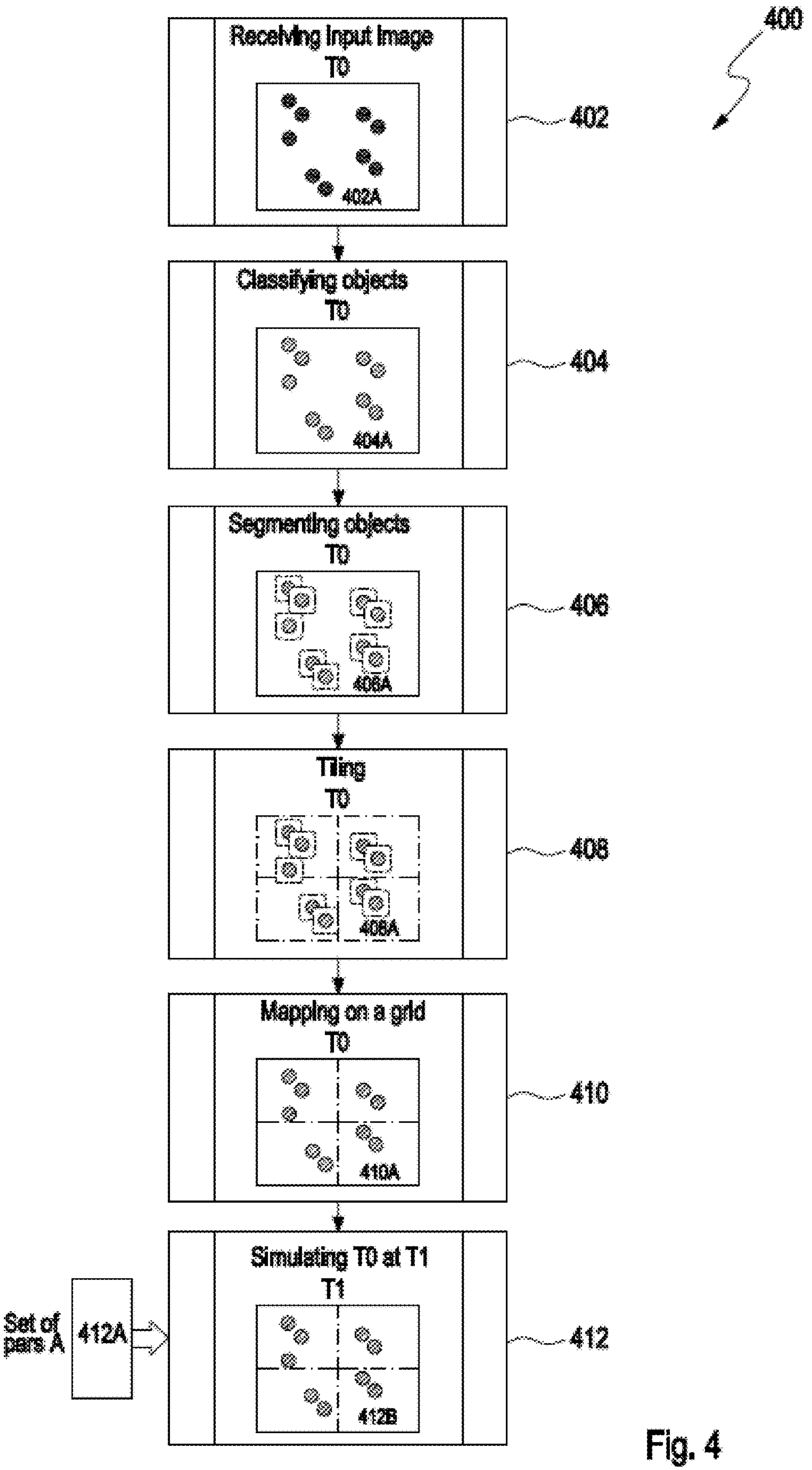
FIG. 4 depicts a flow chart that illustrates an exemplary method for simulating the spatial distribution of objects of interest in digital images via a parameter-based model optimized using for example a spatial agreement measure, in accordance with an embodiment of the disclosure.

FIG. 4 depicts a flow chart that illustrates an exemplary method for simulating the spatial distribution of objects of interest in digital images via a parameter-based model optimized using for example a spatial agreement measure, in accordance with an embodiment of the disclosure. With reference to FIG. 4, an exemplary flow chart 400 is shown.

At 402 at least one input image 402A can be received, wherein the image comprises one or more objects of interest captured at a point in time T0. The input image can be a digitized image from a biopsy of one tumor patient.

At 404, a first machine-learning model can be executed. The machine-learning model can be fed with the input image to classify the one or more objects of interest. In FIG. 4, the input image with classified objects of interest is indicated as 404A. The machine-learning model can be an Artificial Neural Network (ANN), a Deep Neural Network (DNN), and/or a chain of DNNs. In some embodiments, the machine-learning model can comprise a Convolutional Neural Network (CNN), and/or a chain of CNNs. The one or more objects of interest can be tumor cells and/or immune cells. Immune cells can be cytotoxic CD8+ T-cells, proliferating or non proliferating. The tumor cells can be proliferating, and can be expressing Ki67 as the marker of cell proliferation.

At 406, a second machine-learning model can be executed. The machine-learning model can be fed with the input image to segment the one or more objects of interest. In FIG. 4, the input image with classified and segmented objects of interest is indicated as 406A. The machine-learning model can be an Artificial Neural Network (ANN), a Deep Neural Network (DNN), and/or a chain of DNNs. In some embodiments, the machine-learning model can comprise a Convolutional Neural Network (CNN), and/or a chain of CNNs. In some embodiments, the machine-learning model can comprise Region-based CNNs (R-CNNs), Fast or Faster R-CNNs and/or Mask R-CNNs. In some embodiments, 404 and 406 can be performed by a single machine-learning model.

At 408, a tiling algorithm can be executed. The input image can be divided into minimally overlapping square tiles. In FIG. 4, the input image with classified objects of interest divided in tiles is indicated as 408A. The tile overlap can be set to be smaller or equal to 10% of the tile size. When the one or more objects of interest are tumor or immune cells, with CD8+ T-cells having a width of approximately 5 micrometers, the tile size can be set to 100×100 immune cell widths.

At 410, a mapping algorithm can be executed. The tiles obtained at 408 can be mapped on a grid, with each object of interest located on a grid site. In FIG. 4, the input image with classified objects of interest divided in tiles and mapped on a grid is indicated as 410A. When the one or more objects of interest are tumor or immune cells, with CD8+ T-cells having a width of approximately 5 micrometers, the size of each grid cell can be set equal to the immune cell width. The mapping algorithm stores the position of the tumor and immune cells on the grid, as well as physiological properties of the cells, including but not limited to proliferation capacity and stem cellness.

At 412, a parameter-based model can be fed with the mapped tiles of the input image 410A captured at time point T0 and used to simulate the positions of the objects within the mapped tiles of the input image at a different time point, for example T1. Simulated images can be generated and stored at 24 hours intervals. In the parameter-based model at 412, each object can proliferate, migrate, die or interact with other objects according to probabilistic rules. The likelihood of an object to perform an action can be calculated based on probability distributions and its local neighbourhood. When the one or more objects of interest are tumor or immune cells, in order for an immune cell to kill a tumor cell they must be for example in physical proximity. The model parameters can be those related to immune cell dynamics, including but not limited to immune cell proliferation, natural death, killing as well as the randomness of cell migration and the influx rate of immune cells. At least one set of parameter values 412A can be used to define the parameter-based model. In FIG. 4, the image resulting from the simulation with the set of parameter values 412A is indicated as 412B.

Figure 5:
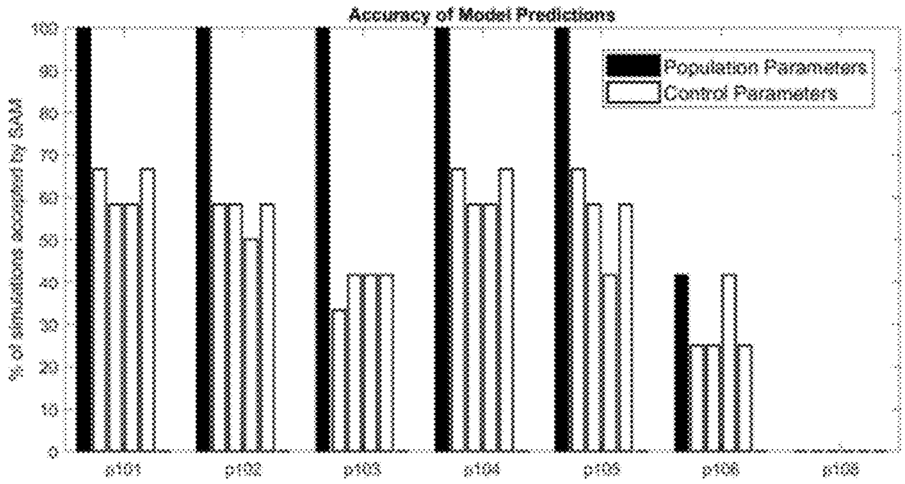
FIG. 5 illustrates the accuracy of the results obtained by applying a parameter-based model optimized using for example a spatial agreement measure to simulate the spatial distribution of immune cells in six tumor patients within oncology clinical trials.

FIG. 5 illustrates the accuracy of the results obtained by applying a parameter-based model optimized using for example a spatial agreement measure to simulate the spatial distribution of immune cells in six tumor patients within oncology clinical trials. The model used is based on the 12 highest-ranking sets of parameter values, also known as population parameters, for the chosen four parameters related to immune cell proliferation, natural death, killing and randomness of immune cell migration. The accuracy obtained with these settings amounts to 77% averaged over the patient data in the test dataset.

Example 1

Model Application: Biopsy Scheduling

Figure 6:
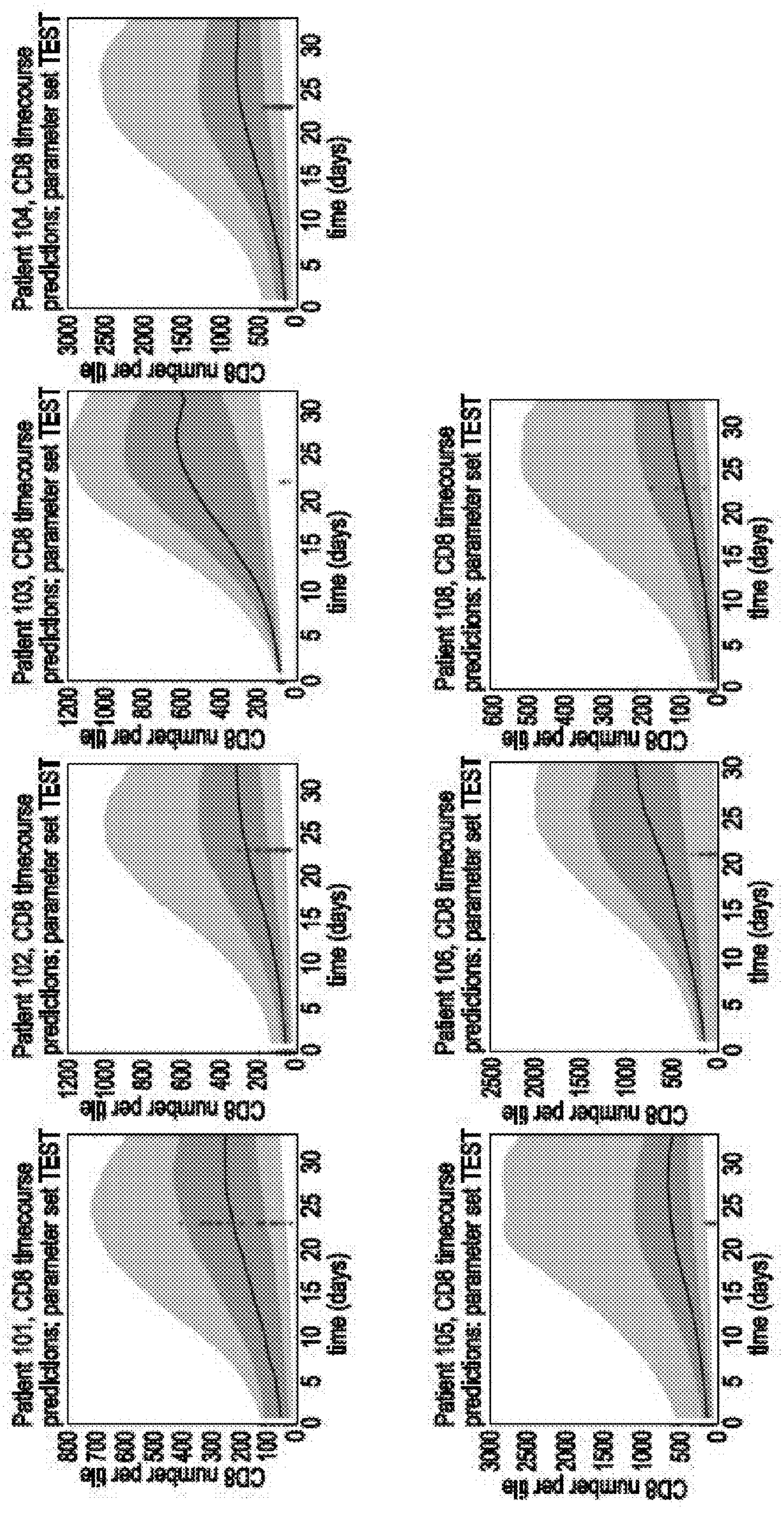
FIG. 6 illustrates the predicted immune cell time course for six tumor patients within oncology clinical trials.

FIG. 6 illustrates the predicted immune cell time course for six tumor patients within oncology clinical trials. For some patients, the model predicts that the number of CD8 cells levels off or begins to decrease after 30 days, whereas for other patients, the number of CD8 cells continues to increase. Depending on the purpose of biopsy collection, drug development teams may choose to propose a cohort or personalised approach for biopsy collection. Simulations generated with this model can be used to inform the optimal time point for biopsy collection in both cases.

Example 2

Model Application: Comparing Monotherapy and Combination Therapies

Figure 7:
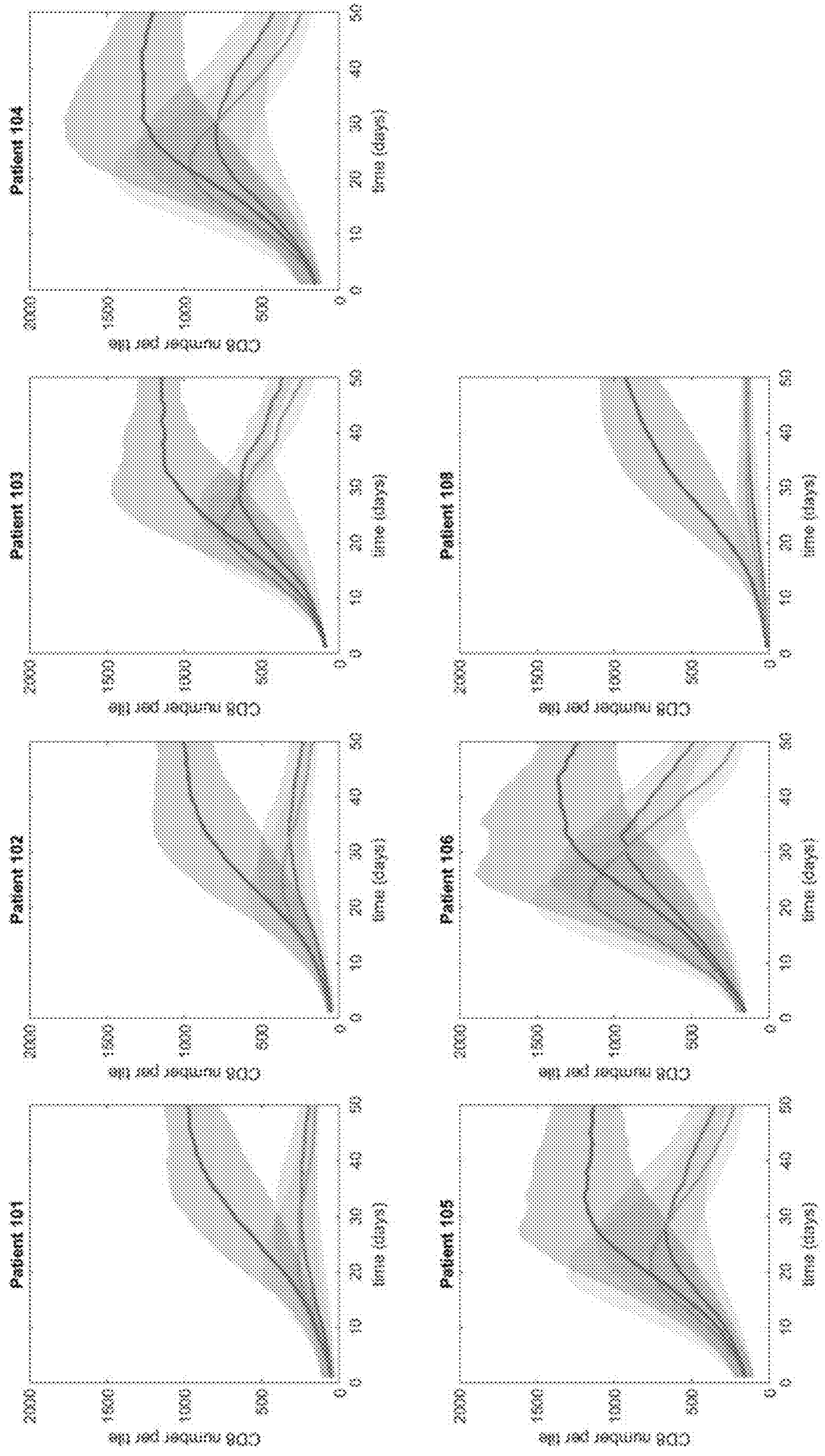
FIG. 7 illustrates the predicted immune cell time course for six tumor patients with three scenarios: a monotherapy and two hypothetical therapy combinations.

FIG. 7 illustrates the predicted immune cell time course for six tumor patients with three scenarios: a monotherapy (scenario 1, blue line) and two hypothetical therapy combinations. The first hypothetical combination partner (scenario 2, orange line) increases the proliferation probability of CD8 cells and the second (scenario 3, pink line) leads to an increase in CD8 influx into the tumour. While both hypothetical drugs lead to an initial increase in CD8 cell number compared to the initial scenario, the molecule that increases the proliferation of CD8 cells, perhaps counterintuitively, leads to a later decrease in CD8 cell number. In contrast the molecule that increases the influx rate of CD8 cells leads to a sustained increase in CD8 cell number. These emergent phenomena are a major reason to use mathematical and computational models to explore complex biological processes.

In the following, further particular embodiments of the present disclosure are listed.

In an embodiment, a computer-implemented method for optimizing the parameter values of a parameter-based model is disclosed, comprising the steps of:

a) receiving (302) at least two digital images, wherein the at least two digital images comprise the same one or more objects of interest captured at different points in time;

b) classifying (304) using a first machine-learning algorithm the one or more objects of interest in the received images;

c) segmenting (306) using a second machine-learning algorithm the classified one or more objects of interest in the received images;

d) obtaining using a tiling algorithm (308) tiles of the received digital images comprising the classified and segmented one or more objects of interest;

e) mapping on a grid using a mapping algorithm (310) the obtained tiles of the received digital images comprising the classified and segmented one or more objects of interest;

f) extracting the radial distribution function (312) of the classified and segmented one or more objects of interest in the mapped tiles of the received one or more digital images other than the received digital image captured at the first point in time;

g) simulating at several points in time using the parameter-based model (314) with at least one set of parameter values (314A) the classified and segmented one or more objects of interest in the mapped tiles of the received digital image captured at the first point in time, wherein the several points in time comprise the points in time at which the received one or more digital images are captured for which the radial distribution function is extracted;

h) extracting the radial distribution functions (316) of the classified and segmented one or more objects of interest in the mapped tiles simulated at the several points in time with the at least one set of parameter values;

i) calculating a spatial agreement measure (318) based on the overlap at corresponding points in time of the extracted radial distribution function of the classified and segmented one or more objects of interest in the mapped tiles simulated with at least one set of parameter values and of the extracted radial distribution function of the classified and segmented one or more objects of interest in the mapped tiles of the received digital images;

j) assigning (320) the at least one set of parameter values to the spatial agreement measure calculated for each of the at least one set of parameter values of the parameter-based model;

k) selecting (322) the optimal set of parameter values, wherein the optimal set of parameter values corresponds to the set of parameter values assigned to the maximum spatial agreement measured calculated.

In an embodiment, a computer-implemented method for optimizing the parameter values of a parameter-based model is disclosed, consisting of the steps of:

a) receiving (302) at least two digital images, wherein the at least two digital images comprise the same one or more objects of interest captured at different points in time;

b) classifying (304) using a first machine-learning algorithm the one or more objects of interest in the received images;

c) segmenting (306) using a second machine-learning algorithm the classified one or more objects of interest in the received images;

d) obtaining using a tiling algorithm (308) tiles of the received digital images comprising the classified and segmented one or more objects of interest;

e) mapping on a grid using a mapping algorithm (310) the obtained tiles of the received digital images comprising the classified and segmented one or more objects of interest;

f) extracting the radial distribution function (312) of the classified and segmented one or more objects of interest in the mapped tiles of the received one or more digital images other than the received digital image captured at the first point in time;

g) simulating at several points in time using the parameter-based model (314) with at least one set of parameter values (314A) the classified and segmented one or more objects of interest in the mapped tiles of the received digital image captured at the first point in time, wherein the several points in time comprise the points in time at which the received one or more digital images are captured for which the radial distribution function is extracted;

h) extracting the radial distribution functions (316) of the classified and segmented one or more objects of interest in the mapped tiles simulated at the several points in time with the at least one set of parameter values;

i) calculating a spatial agreement measure (318) based on the overlap at corresponding points in time of the extracted radial distribution function of the classified and segmented one or more objects of interest in the mapped tiles simulated with at least one set of parameter values and of the extracted radial distribution function of the classified and segmented one or more objects of interest in the mapped tiles of the received digital images;

j) assigning (320) the at least one set of parameter values to the spatial agreement measure calculated for each of the at least one set of parameter values of the parameter-based model;

k) selecting (322) the optimal set of parameter values, wherein the optimal set of parameter values corresponds to the set of parameter values assigned to the maximum spatial agreement measure calculated.

In another embodiment, the method according to any of the embodiments 1-2 is disclosed, wherein a subset of the steps of the embodiments 1-2 is performed.

In another embodiment, the method according to any of the embodiments 1-3 is disclosed, wherein the steps of the embodiments 1-3 are performed sequentially.

In another embodiment, the method according to any of the embodiments 1-4 is disclosed, wherein the received at least two digital images are digitized images of paired biopsies, wherein the paired biopsies are obtained at different points in time.

In another embodiment, the method according to embodiment 5 is disclosed, wherein the different points in time correspond to pre-treatment and on-treatment in the course of a therapy.

In another embodiment, the method according to any of the embodiments 1-6 is disclosed, wherein the one or more objects of interest comprise tumor cells and/or immune cells.

In another embodiment, the method according to any of the embodiments 1-7 is disclosed, wherein the one or more objects of interest in the received at least two digital images comprise tumor cells and/or immune cells, and wherein the immune cells are CD8+ T-cells.

In another embodiment, the method according to any of the embodiments 1-7 is disclosed, wherein the one or more objects of interest in the received at least two digital images comprise tumor cells and/or immune cells, and wherein the tumor cells express the marker Ki67.

In an embodiment, a method according to any of the embodiments 1-9 is disclosed, wherein the steps of classifying and segmenting the one or more objects of interest in the received images are performed in parallel.

In an embodiment, a method according to any of the embodiments 1-9 is disclosed, wherein the steps of classifying and segmenting the one or more objects of interest in the received images are performed using a single machine-learning algorithm.

In an embodiment, a method according to any of the embodiments 1-11 is disclosed, wherein the tiling algorithm selects minimally overlapping square tiles, and/or wherein the tiles have dimensions of 100×100 object size and/or wherein the tile overlap is less or equal to 10%.

In an embodiment, a method according to any of the embodiments 1-12 is disclosed, wherein the radial distribution function is extracted by computing the total number of objects at each radius on the mapped tiles normalized by the mean density of objects on the mapped tiles.

In an embodiment, a method according to any of the embodiments 1-13 is disclosed, wherein the radial distribution functions are extracted by computing the total number of objects normalized by the mean density of objects on the mapped tiles.

In an embodiment, a method according to claim 14, wherein the distance between objects is computed as the Chebyshev radial distance.

In an embodiment, a method according to any of the embodiments 1-15 is disclosed, wherein the parameter-based model is based on at least four parameters.

In an embodiment, a method according to any of the embodiments 1-16 is disclosed, wherein the simulation is performed with at least 1000 sets of parameter values.

In an embodiment, a method according to any of the embodiments 7-17 is disclosed, wherein the parameter-based model is based on at least four parameters, and wherein the at least four parameters comprise the probability of immune cell proliferation, killing, natural death and the randomness of the immune cell migration.

In an embodiment, a method according to any of the embodiments 1-18 is disclosed, wherein the spatial agreement measure is calculated as the proportion of the distances for which more than 80% of radial distribution function values of the simulated one or more objects in the mapped tiles fit within the range approximately of 20% of the radial distribution function values of the classified and segmented one or more objects in the received tiles.

In an embodiment, a method according to embodiment 19 is disclosed, wherein a second spatial agreement measure is calculated as the ratio of the ranges of radial distribution function values of simulated and observed tiles within the first 15 distance units.

In an embodiment, a method according to any of the embodiments 1-20 is disclosed, wherein more than one optimal set of parameter values is selected, and wherein each optimal set of parameter values has assigned spatial agreement measure greater than 0.7.

In an embodiment, a method according to embodiment 21 is disclosed, wherein at least 12 optimal sets of parameter values are selected.

In an embodiment, a computer-implemented method is disclosed, comprising the steps of:

- a') receiving (402) at least one digital image comprising one or more objects of interest captured at a first point in time;
- b') classifying (404) using a first machine-learning algorithm the one or more objects of interest in the received digital image;
- c') segmenting (406) using a second machine-learning algorithm the classified one or more objects of interest in the received digital image;
- d') obtaining using a tiling algorithm (408) tiles of the received digital image comprising the classified and segmented one or more objects of interest;
- e') mapping on a grid using a mapping algorithm (410) the obtained tiles of the received digital image comprising the classified and segmented one or more objects of interest;
- f) simulating at one or more points in time using a parameter-based model (412) optimized according to the method of any of the embodiments 1-22 the spatial distribution of the classified and segmented one or more objects of interest in the mapped tiles of the received digital image, wherein the one or more points in time differ from the first point in time at which the received digital image is captured.

In an embodiment, a computer-implemented method is disclosed, consisting of the steps of:

- a') receiving (402) at least one digital image comprising one or more objects of interest captured at a first point in time;
- b') classifying (404) using a first machine-learning algorithm the one or more objects of interest in the received digital image;
- c') segmenting (406) using a second machine-learning algorithm the classified one or more objects of interest in the received digital image;
- d') obtaining using a tiling algorithm (408) tiles of the received digital image comprising the classified and segmented one or more objects of interest;
- e') mapping on a grid using a mapping algorithm (410) the obtained tiles of the received digital image comprising the classified and segmented one or more objects of interest;
- f) simulating at one or more points in time using a parameter-based model (412) optimized according to the method of any of the embodiments 1-22 the spatial distribution of the classified and segmented one or more objects of interest in the mapped tiles of the received digital image, wherein the one or more points in time differ from the first point in time at which the received digital image is captured.

In another embodiment, the method according to any of the embodiments 23-24 is disclosed, wherein a subset of the steps of the embodiments 23-24 is performed.

In another embodiment, the method according to any of the embodiments 23-25 is disclosed, wherein the steps of the embodiments 23-25 are performed sequentially.

In another embodiment, the method according to any of the embodiments 23-26 is disclosed, wherein the at least one digital image is a digitized image of a biopsy.

In another embodiment, the method according to any of the embodiments 23-27 is disclosed, wherein the one or more objects of interest comprise tumor cells and/or immune cells.

In another embodiment, the method according to any of the embodiments 23-28 is disclosed, wherein the one or more objects of interest in the received digital image comprise tumor cells and/or immune cells, and wherein the immune cells are CD8+ T-cells.

In another embodiment, the method according to any of the embodiments 23-28 is disclosed, wherein the one or more objects of interest in the received digital image comprise tumor cells and/or immune cells, and wherein the tumor cells express the marker Ki67.

In an embodiment, a method according to any of the embodiments 23-30 is disclosed, wherein the steps of classifying and segmenting the one or more objects of interest in the received image are performed in parallel.

In an embodiment, a method according to any of the embodiments 23-30 is disclosed, wherein the steps of classifying and segmenting the one or more objects of interest in the received image are performed using a single machine-learning algorithm.

In an embodiment, a method according to any of the embodiments 23-32 is disclosed, wherein the tiling algorithm selects minimally overlapping square tiles, and/or wherein the tiles have dimensions of 100×100 object size and/or wherein the tile overlap is less or equal to 10%.

In an embodiment, a method according to any of the embodiments 23-33 is disclosed, wherein the wherein the parameter-based model is based on at least four parameters.

In an embodiment, a method according to any of the embodiments 28-34 is disclosed, wherein the parameter-based model is based on at least four parameters, and wherein the at least four parameters comprise the probability of immune cell proliferation, killing, natural death and the randomness of the immune cell migration.

In an embodiment, a method according to any of embodiments 28-33 is disclosed, wherein the simulated one or more objects in the mapped tiles at one or more points in time allows for suggesting biopsy scheduling on a personalized and/or cohort basis, and/or allows for predicting the effect of different cancer immunotherapies or combinations thereof.

In an embodiment, a computer program product is disclosed comprising instructions which, when the program is executed by a computer, cause the computer to carry out the steps of:

a) receiving at least two digital images, wherein the at least two digital images comprise the same one or more objects of interest captured at different points in time;
b) classifying using a first machine-learning algorithm the one or more objects of interest in the received images;
c) segmenting using a second machine-learning algorithm the classified one or more objects of interest in the received images;
d) obtaining using a tiling algorithm tiles of the received digital images comprising the classified and segmented one or more objects of interest;
e) mapping on a grid using a mapping algorithm the obtained tiles of the received digital images comprising the classified and segmented one or more objects of interest;
f) extracting the radial distribution function of the classified and segmented one or more objects of interest in the mapped tiles of the received one or more digital images other than the received digital image captured at the first point in time;
g) simulating at several points in time using the parameter-based model with at least one set of parameter values the classified and segmented one or more objects of interest in the mapped tiles of the received digital image captured at the first point in time, wherein the several points in time comprise the points in time at which the received one or more digital images are captured for which the radial distribution function is extracted;
h) extracting the radial distribution functions of the classified and segmented one or more objects of interest in the mapped tiles simulated at the several points in time with the at least one set of parameter values;
i) calculating a spatial agreement measure based on the overlap at corresponding points in time of the extracted radial distribution function of the classified and segmented one or more objects of interest in the mapped tiles simulated with at least one set of parameter values and of the extracted radial distribution function of the classified and segmented one or more objects of interest in the mapped tiles of the received digital images;
j) assigning the at least one set of parameter values to the spatial agreement measure calculated for each of the at least one set of parameter values of the parameter-based model;
k) selecting the optimal set of parameter values, wherein the optimal set of parameter values corresponds to the set of parameter values assigned to the maximum spatial agreement measure calculated.

In an embodiment, a computer program product is disclosed consisting of instructions which, when the program is executed by a computer, cause the computer to carry out the steps of:

a) receiving at least two digital images, wherein the at least two digital images comprise the same one or more objects of interest captured at different points in time;
b) classifying using a first machine-learning algorithm the one or more objects of interest in the received images;
c) segmenting using a second machine-learning algorithm the classified one or more objects of interest in the received images;
d) obtaining using a tiling algorithm tiles of the received digital images comprising the classified and segmented one or more objects of interest;
e) mapping on a grid using a mapping algorithm the obtained tiles of the received digital images comprising the classified and segmented one or more objects of interest;
f) extracting the radial distribution function of the classified and segmented one or more objects of interest in the mapped tiles of the received one or more digital images other than the received digital image captured at the first point in time;
g) simulating at several points in time using the parameter-based model with at least one set of parameter values the classified and segmented one or more objects of interest in the mapped tiles of the received digital image captured at the first point in time, wherein the several points in time comprise the points in time at which the received one or more digital images are captured for which the radial distribution function is extracted;

h) extracting the radial distribution functions of the classified and segmented one or more objects of interest in the mapped tiles simulated at the several points in time with the at least one set of parameter values;

i) calculating a spatial agreement measure based on the overlap at corresponding points in time of the extracted radial distribution function of the classified and segmented one or more objects of interest in the mapped tiles simulated with at least one set of parameter values and of the extracted radial distribution function of the classified and segmented one or more objects of interest in the mapped tiles of the received digital images;

j) assigning the at least one set of parameter values to the spatial agreement measure calculated for each of the at least one set of parameter values of the parameter-based model;

k) selecting the optimal set of parameter values, wherein the optimal set of parameter values corresponds to the set of parameter values assigned to the maximum spatial agreement measure calculated.

A computer-readable storage medium comprising instructions which, when the program is executed by a computer, cause the computer to carry out the steps of:

a) receiving at least two digital images, wherein the at least two digital images comprise the same one or more objects of interest captured at different points in time;

b) classifying using a first machine-learning algorithm the one or more objects of interest in the received images;

c) segmenting using a second machine-learning algorithm the classified one or more objects of interest in the received images;

d) obtaining using a tiling algorithm tiles of the received digital images comprising the classified and segmented one or more objects of interest;

e) mapping on a grid using a mapping algorithm the obtained tiles of the received digital images comprising the classified and segmented one or more objects of interest;

f) extracting the radial distribution function of the classified and segmented one or more objects of interest in the mapped tiles of the received one or more digital images other than the received digital image captured at the first point in time;

g) simulating at several points in time using the parameter-based model with at least one set of parameter values the classified and segmented one or more objects of interest in the mapped tiles of the received digital image captured at the first point in time, wherein the several points in time comprise the points in time at which the received one or more digital images are captured for which the radial distribution function is extracted;

h) extracting the radial distribution functions of the classified and segmented one or more objects of interest in the mapped tiles simulated at the several points in time with the at least one set of parameter values;

i) calculating a spatial agreement measure based on the overlap at corresponding points in time of the extracted radial distribution function of the classified and segmented one or more objects of interest in the mapped tiles simulated with at least one set of parameter values and of the extracted radial distribution function of the classified and segmented one or more objects of interest in the mapped tiles of the received digital images;

j) assigning the at least one set of parameter values to the spatial agreement measure calculated for each of the at least one set of parameter values of the parameter-based model;

k) selecting the optimal set of parameter values, wherein the optimal set of parameter values corresponds to the set of parameter values assigned to the maximum spatial agreement measure calculated.

A computer-readable storage medium consisting of instructions which, when the program is executed by a computer, cause the computer to carry out the steps of:

a) receiving at least two digital images, wherein the at least two digital images comprise the same one or more objects of interest captured at different points in time;

b) classifying using a first machine-learning algorithm the one or more objects of interest in the received images;

c) segmenting using a second machine-learning algorithm the classified one or more objects of interest in the received images;

d) obtaining using a tiling algorithm tiles of the received digital images comprising the classified and segmented one or more objects of interest;

e) mapping on a grid using a mapping algorithm the obtained tiles of the received digital images comprising the classified and segmented one or more objects of interest;

f) extracting the radial distribution function of the classified and segmented one or more objects of interest in the mapped tiles of the received one or more digital images other than the received digital image captured at the first point in time;

g) simulating at several points in time using the parameter-based model with at least one set of parameter values the classified and segmented one or more objects of interest in the mapped tiles of the received digital image captured at the first point in time, wherein the several points in time comprise the points in time at which the received one or more digital images are captured for which the radial distribution function is extracted;

h) extracting the radial distribution functions of the classified and segmented one or more objects of interest in the mapped tiles simulated at the several points in time with the at least one set of parameter values;

i) calculating a spatial agreement measure based on the overlap at corresponding points in time of the extracted radial distribution function of the classified and segmented one or more objects of interest in the mapped tiles simulated with at least one set of parameter values and of the extracted radial distribution function of the classified and segmented one or more objects of interest in the mapped tiles of the received digital images;

j) assigning the at least one set of parameter values to the spatial agreement measure calculated for each of the at least one set of parameter values of the parameter-based model;

k) selecting the optimal set of parameter values, wherein the optimal set of parameter values corresponds to the set of parameter values assigned to the maximum spatial agreement measure calculated.

A system comprising:

an input/output (I/O) unit (202) configured to receive at least two digital images, wherein the at least two digital images comprise the same one or more objects of interest captured at different points in time; and a processor (204), configured to perform the steps of:

i. classifying using a first machine-learning algorithm the one or more objects of interest in the received images;

ii. segmenting using a second machine-learning algorithm the classified one or more objects of interest in the received images;

iii. obtaining using a tiling algorithm tiles of the received digital images comprising the classified and segmented one or more objects of interest;

iv. mapping on a grid using a mapping algorithm the obtained tiles of the received digital images comprising the classified and segmented one or more objects of interest;

v. extracting the radial distribution function of the classified and segmented one or more objects of interest in the mapped tiles of the received one or more digital images other than the received digital image captured at the first point in time;

vi. simulating at several points in time using the parameter-based model with at least one set of parameter values the classified and segmented one or more objects of interest in the mapped tiles of the received digital image captured at the first point in time, wherein the several points in time comprise the points in time at which the received one or more digital images are captured for which the radial distribution function is extracted;

vii. extracting the radial distribution functions of the classified and segmented one or more objects of interest in the mapped tiles simulated at the several points in time with the at least one set of parameter values;

viii. calculating a spatial agreement measure based on the overlap at corresponding points in time of the extracted radial distribution function of the classified and segmented one or more objects of interest in the mapped tiles simulated with at least one set of parameter values and of the extracted radial distribution function of the classified and segmented one or more objects of interest in the mapped tiles of the received digital images;

ix. assigning the at least one set of parameter values to the spatial agreement measure calculated for each of the at least one set of parameter values of the parameter-based model;

x. selecting the optimal set of parameter values, wherein the optimal set of parameter values corresponds to the set of parameter values assigned to the maximum spatial agreement measure calculated.

A system consisting of:

an input/output (I/O) unit (202) configured to receive at least two digital images, wherein the at least two digital images comprise the same one or more objects of interest captured at different points in time; and a processor (204), configured to perform the steps of:

i. classifying using a first machine-learning algorithm the one or more objects of interest in the received images;

ii. segmenting using a second machine-learning algorithm the classified one or more objects of interest in the received images;

iii. obtaining using a tiling algorithm tiles of the received digital images comprising the classified and segmented one or more objects of interest;

iv. mapping on a grid using a mapping algorithm the obtained tiles of the received digital images comprising the classified and segmented one or more objects of interest;

v. extracting the radial distribution function of the classified and segmented one or more objects of interest in the mapped tiles of the received one or more digital images other than the received digital image captured at the first point in time;

vi. simulating at several points in time using the parameter-based model with at least one set of parameter values the classified and segmented one or more objects of interest in the mapped tiles of the received digital image captured at the first point in time, wherein the several points in time comprise the points in time at which the received one or more digital images are captured for which the radial distribution function is extracted;

vii. extracting the radial distribution functions of the classified and segmented one or more objects of interest in the mapped tiles simulated at the several points in time with the at least one set of parameter values;

viii. calculating a spatial agreement measure based on the overlap at corresponding points in time of the extracted radial distribution function of the classified and segmented one or more objects of interest in the mapped tiles simulated with at least one set of parameter values and of the extracted radial distribution function of the classified and segmented one or more objects of interest in the mapped tiles of the received digital images;

ix. assigning the at least one set of parameter values to the spatial agreement measure calculated for each of the at least one set of parameter values of the parameter-based model;

x. selecting the optimal set of parameter values, wherein the optimal set of parameter values corresponds to the set of parameter values assigned to the maximum spatial agreement measure calculated.

In an embodiment, a computer program product is disclosed comprising instructions which, when the program is executed by a computer, cause the computer to carry out the steps of:

a') receiving at least one digital image comprising one or more objects of interest captured at a first point in time;

b') classifying using a first machine-learning algorithm the one or more objects of interest in the received digital image;

c') segmenting using a second machine-learning algorithm the classified one or more objects of interest in the received digital image;

d') obtaining using a tiling algorithm tiles of the received digital image comprising the classified and segmented one or more objects of interest;

e') mapping on a grid using a mapping algorithm the obtained tiles of the received digital image comprising the classified and segmented one or more objects of interest;

f') simulating at one or more points in time using a parameter-based model optimized according to the method of any of the embodiments 1-21 the spatial distribution of the classified and segmented one or more objects of interest in the mapped tiles of the received digital image, wherein the one or more points in time differ from the first point in time at which the received digital image is captured.

In an embodiment, a computer program product is disclosed consisting of instructions which, when the program is executed by a computer, cause the computer to carry out the steps of:

a') receiving at least one digital image comprising one or more objects of interest captured at a first point in time;

b') classifying using a first machine-learning algorithm the one or more objects of interest in the received digital image;

c') segmenting using a second machine-learning algorithm the classified one or more objects of interest in the received digital image;

d') obtaining using a tiling algorithm tiles of the received digital image comprising the classified and segmented one or more objects of interest;

e') mapping on a grid using a mapping algorithm the obtained tiles of the received digital image comprising the classified and segmented one or more objects of interest;

f') simulating at one or more points in time using a parameter-based model optimized according to the method of any of the embodiments 1-21 the spatial distribution of the classified and segmented one or more objects of interest in the mapped tiles of the received digital image, wherein the one or more points in time differ from the first point in time at which the received digital image is captured.

A computer-readable storage medium comprising instructions which, when the program is executed by a computer, cause the computer to carry out the steps of:

a') receiving at least one digital image comprising one or more objects of interest captured at a first point in time;

b') classifying using a first machine-learning algorithm the one or more objects of interest in the received digital image;

c') segmenting using a second machine-learning algorithm the classified one or more objects of interest in the received digital image;

d') obtaining using a tiling algorithm tiles of the received digital image comprising the classified and segmented one or more objects of interest;

e') mapping on a grid using a mapping algorithm the obtained tiles of the received digital image comprising the classified and segmented one or more objects of interest;

f') simulating at one or more points in time using a parameter-based model optimized according to the method of any of the embodiments 1-21 the spatial distribution of the classified and segmented one or more objects of interest in the mapped tiles of the received digital image, wherein the one or more points in time differ from the first point in time at which the received digital image is captured.

A computer-readable storage medium consisting of instructions which, when the program is executed by a computer, cause the computer to carry out the steps of:

a') receiving at least one digital image comprising one or more objects of interest captured at a first point in time;

b') classifying using a first machine-learning algorithm the one or more objects of interest in the received digital image;

c') segmenting using a second machine-learning algorithm the classified one or more objects of interest in the received digital image;

d') obtaining using a tiling algorithm tiles of the received digital image comprising the classified and segmented one or more objects of interest;

e') mapping on a grid using a mapping algorithm the obtained tiles of the received digital image comprising the classified and segmented one or more objects of interest;

f') simulating at one or more points in time using a parameter-based model optimized according to the method of any of the embodiments 1-21 the spatial distribution of the classified and segmented one or more objects of interest in the mapped tiles of the received digital image, wherein the one or more points in time differ from the first point in time at which the received digital image is captured.

A system comprising:

an input/output (I/O) unit (202) configured to receive at least one digital image comprising one or more objects of interest captured at a first point in time; and a processor (204), configured to perform the steps of:

a') classifying using a first machine-learning algorithm the one or more objects of interest in the received digital image;

b') segmenting using a second machine-learning algorithm the classified one or more objects of interest in the received digital image;

c') obtaining using a tiling algorithm tiles of the received digital image comprising the classified and segmented one or more objects of interest;

d') mapping on a grid using a mapping algorithm the obtained tiles of the received digital image comprising the classified and segmented one or more objects of interest;

e') simulating at one or more points in time using a parameter-based model optimized according to the method of any of the embodiments 1-21 the spatial distribution of the classified and segmented one or more objects of interest in the mapped tiles of the received digital image, wherein the one or more points in time differ from the first point in time at which the received digital image is captured.

A system consisting of:

an input/output (I/O) unit (202) configured to receive at least one digital image comprising one or more objects of interest captured at a first point in time; and a processor (204), configured to perform the steps of:

a') classifying using a first machine-learning algorithm the one or more objects of interest in the received digital image;

b') segmenting using a second machine-learning algorithm the classified one or more objects of interest in the received digital image;

c') obtaining using a tiling algorithm tiles of the received digital image comprising the classified and segmented one or more objects of interest;

d') mapping on a grid using a mapping algorithm the obtained tiles of the received digital image comprising the classified and segmented one or more objects of interest;

e') simulating at one or more points in time using a parameter-based model optimized according to the method of any of the embodiments 1-21 the spatial distribution of the classified and segmented one or more objects of interest in the mapped tiles of the received digital image, wherein the one or more points in time differ from the first point in time at which the received digital image is captured.

A computer-implemented system or method according to any of the previous embodiments for scheduling biopsies on a personalized or cohort basis.

A computer-implemented system or method according to any of the previous embodiments for predicting the effect of different cancer immunotherapies or combinations of therapies.

While the present invention is described with reference to certain embodiments, it will be understood by those skilled in the art that various changes can be made and equivalents can be substituted without departure from the scope of the present invention. In addition, many modifications can be made to adapt a particular situation or material to the teachings of the present invention without departing from its scope. Therefore, it is intended that the present invention not be limited to the particular embodiments disclosed, but that the present invention will include all embodiments that fall within the scope of the appended claims.

BIBLIOGRAPHY

[1]Barua et al., "Spatial interaction of tumor cells and regulatory T cells correlates with survival in non-small cell lung cancer", Lung Cancer Vol. 117, pagg. 73-79 (2018).

[2]Brown et al., "Quantitative assessment Ki-67 score for prediction of response to neoadjuvant chemotherapy in breast cancer", Lab Invest 94, 98-106 (2014).

[3]Corredor et al., "Spatial architecture and arrangement of tumor-infiltrating lymphocytes for predicting likelihood of recurrence in early-stage non-small cell lung cancer", Clin Cancer Res Vol. 25 1526-1534 (2019).

[4]Saltz et al., "Spatial organization and molecular correlation of tumor-infiltrating lymphocytes using deep learning on pathology images", Cell Rep 23 (1) 181-193 (2018).

[5]Schwen et al., "Data-driven discovery of immune contexture biomarkers", Frontiers in Oncology, Vol. 8 (2018).

[6]Kather et al., "In silico modeling of immunotherapy and stroma-targeting therapies in human colorectal cancer", Cancer Res Vol. 77 6442-6452 (2017).

[7]Norton et al., "Multiscale agent-based and hybrid modeling of the tumor immune microenvironment", Processes (Basel) Vol. 7 (2019).

[8]Gong et al., "A computational multiscale agent-based model for simulating spatio-temporal tumour immune response to PDI and PDLI inhibition", J R Soc Interface Vol. 14 (2017).

[9]Kather et al., "Topography of cancer-associated immune cells in human solid tumors", Elife Vol. 7 (2018).

[10]Alfonso et al., "In-silico insights on the prognostic potential of immune cell infiltration patterns in the breast lobular epithelium", Sci Rep. Vol 6 (2016).

What is claimed is:

1. A computer-implemented method for optimizing one or more parameter values of a parameter-based model, comprising the steps of:

a) receiving (302) at least two digital images, wherein the at least two digital images comprise the same one or more objects of interest captured at different points in time;

b) classifying (304) the one or more objects of interest in the received images;

c) segmenting (306) the classified one or more objects of interest in the received images;

d) obtaining using a tiling algorithm (308) tiles of the received digital images comprising the classified and segmented one or more objects of interest;

e) mapping on a grid using a mapping algorithm (310) the obtained tiles of the received digital images comprising the classified and segmented one or more objects of interest;

f) extracting a radial distribution function (312) of the classified and segmented one or more objects of interest in the mapped tiles of the received one or more digital images other than the received digital image captured at a first point in time;

g) simulating at several points in time using the parameter-based model (314) with at least one set of parameter values (314A) the classified and segmented one or more objects of interest in the mapped tiles of the received digital image captured at the first point in time, wherein the several points in time comprise the points in time at which the received one or more digital images are captured for which the radial distribution function is extracted;

h) extracting the radial distribution functions (316) of the classified and segmented one or more objects of interest in the mapped tiles simulated at the several points in time with the at least one set of parameter values; and i) calculating a spatial agreement measure (318) based on an overlap at corresponding points in time of the extracted radial distribution function of the classified and segmented one or more objects of interest in the mapped tiles simulated with at least one set of parameter values and of the extracted radial distribution function of the classified and segmented one or more objects of interest in the mapped tiles of the received digital images.

2. The method of claim 1, wherein the received at least two digital images are digitized images of paired biopsies, wherein the paired biopsies are obtained at different points in time.

3. The method of claim 2, wherein the different points in time correspond to pre-treatment and on-treatment in a course of a therapy.

4. The method of claim 1, wherein the one or more objects of interest comprise tumor cells and/or immune cells.

5. The method of claim 4, wherein the parameter-based model is based on at least four parameters, and wherein the at least four parameters comprise a probability of immune cell proliferation, a probability of immune cell killing, a probability of immune cell natural death, and a randomness of immune cell migration.

6. The method of claim 4, wherein the immune cells comprise CD8+ T-cells.

7. The method of claim 4, wherein the tumor cells express marker Ki67.

8. The method of claim 1, wherein the radial distribution functions are extracted by computing a total number of objects normalized by a mean density of objects on the mapped tiles.

9. The method of claim 1, further comprising:

assigning (320) the at least one set of parameter values to the spatial agreement measure calculated for each of the at least one set of parameter values of the parameter-based model; and selecting (322) a set of parameter values, wherein the set of parameter values corresponds to a set of parameter values assigned to a maximum spatial agreement measure calculated.

10. The method of claim 1, further comprising:

classifying (304) using a first machine-learning algorithm the one or more objects of interest in the received images; and segmenting (306) using a second machine-learning algorithm the classified one or more objects of interest in the received images.

11. The method of claim 1, wherein the steps of classifying and segmenting the one or more objects of interest in the received images are performed in parallel.

12. The method of claim 1, wherein the steps of classifying and segmenting the one or more objects of interest in the received images are performed using a single machine-learning algorithm.

13. The method of claim 1, wherein the parameter-based model is based on at least four parameters.

14. The method of claim 1, wherein the simulation is performed with at least 1000 sets of parameter values.

15. A non-transitory computer-readable storage medium comprising instructions for optimizing one or more parameter values of a parameter-based model which, when the instructions are executed by a computer, cause the computer to carry out the steps of:

a) receiving at least two digital images, wherein the at least two digital images comprise the same one or more objects of interest captured at different points in time;

b) classifying using a first machine-learning algorithm the one or more objects of interest in the received images;

c) segmenting using a second machine-learning algorithm the classified one or more objects of interest in the received images;

d) obtaining using a tiling algorithm tiles of the received digital images comprising the classified and segmented one or more objects of interest;

e) mapping on a grid using a mapping algorithm the obtained tiles of the received digital images comprising the classified and segmented one or more objects of interest;

f) extracting a radial distribution function of the classified and segmented one or more objects of interest in the mapped tiles of the received one or more digital images other than the received digital image captured at a first point in time;

g) simulating at several points in time using the parameter-based model with at least one set of parameter values the classified and segmented one or more objects of interest in the mapped tiles of the received digital image captured at the first point in time, wherein the several points in time comprise the points in time at which the received one or more digital images are captured for which the radial distribution function is extracted;

h) extracting the radial distribution functions of the classified and segmented one or more objects of interest in the mapped tiles simulated at the several points in time with the at least one set of parameter values;

i) calculating a spatial agreement measure based on an overlap at corresponding points in time of the extracted radial distribution function of the classified and segmented one or more objects of interest in the mapped tiles simulated with at least one set of parameter values and of the extracted radial distribution function of the classified and segmented one or more objects of interest in the mapped tiles of the received digital images;

j) assigning the at least one set of parameter values to the spatial agreement measure calculated for each of the at least one set of parameter values of the parameter-based model; and k) selecting a set of parameter values, wherein the set of parameter values corresponds to a set of parameter values assigned to a maximum spatial agreement measure calculated.

16. A computer-implemented method, comprising the steps of:

a') receiving (402) at least one digital image comprising one or more objects of interest captured at a first point in time;

b') classifying (404) the one or more objects of interest in the received digital image;

c') segmenting (406) the classified one or more objects of interest in the received digital image;

d') obtaining using a tiling algorithm (408) tiles of the received digital image comprising the classified and segmented one or more objects of interest;

e') mapping on a grid using a mapping algorithm (410) the obtained tiles of the received digital image comprising the classified and segmented one or more objects of interest; and f') simulating at one or more points in time using a parameter-based model (412) a spatial distribution of the classified and segmented one or more objects of interest in the mapped tiles of the received digital image, wherein one or more parameters of the parameter-based model are calibrated based on a correspondence between simulated spatial distributions and spatial distributions extracted from classified and segmented objects of interest in one or more training digital images.

17. The method of claim 16, wherein the received at least one digital image is a digitized image of a biopsy.

18. The method of claim 17, wherein the one or more objects of interest comprise tumor cells and/or immune cells.

19. The method of claim 16, further comprising:

classifying (404) using a first machine-learning algorithm the one or more objects of interest in the received images; and segmenting (406) using a second machine-learning algorithm the classified one or more objects of interest in the received images.

20. The method of claim 16, wherein the one or more points in time differ from the first point in time at which the received digital image is captured.

* * * * *